United States Patent
Radermacher

(10) Patent No.: US 8,075,180 B2
(45) Date of Patent: Dec. 13, 2011

(54) RAPID AND EASY BOTTLE TEST

(75) Inventor: Fabienne Radermacher, Obaix (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 89 days.

(21) Appl. No.: 12/522,039

(22) PCT Filed: Jan. 24, 2008

(86) PCT No.: PCT/EP2008/050784
§ 371 (c)(1),
(2), (4) Date: Jul. 2, 2009

(87) PCT Pub. No.: WO2008/090189
PCT Pub. Date: Jul. 31, 2008

(65) Prior Publication Data
US 2009/0310647 A1 Dec. 17, 2009

(30) Foreign Application Priority Data
Jan. 25, 2007 (EP) .................. 07101134

(51) Int. Cl.
*G01N 25/00* (2006.01)
(52) U.S. Cl. .............. 374/57; 374/5; 374/43; 374/55
(58) Field of Classification Search ............ 374/45, 374/57, 5, 43, 55
See application file for complete search history.

(56) References Cited

U.S. PATENT DOCUMENTS

| | | | |
|---|---|---|---|
| 4,733,973 A * | 3/1988 | Machak et al. | 374/5 |
| 4,888,148 A | 12/1989 | Hartitz | |
| 6,727,317 B2 * | 4/2004 | Kurja et al. | 524/582 |
| 2003/0047565 A1 * | 3/2003 | Oda et al. | 220/660 |
| 2009/0120900 A1 * | 5/2009 | Mitadera et al. | 215/382 |

* cited by examiner

*Primary Examiner* — Gail Verbitsky
*Assistant Examiner* — Mirellys Jagan

(57) ABSTRACT

A method for predicting the drop impact resistance of a stretch-blow molded polypropylene container which comprises the steps of measuring the initial size of the container, placing it in an oven, remeasuring its size after removing it from the oven, calculating the percentage difference in size of the container and determining its drop impact resistance, which is proportional to said difference.

10 Claims, 1 Drawing Sheet

RAPID AND EASY BOTTLE TEST

CROSS-REFERENCE TO RELATED APPLICATIONS

This application claims the benefit of PCT/EP2008/050784, filed Jan. 24, 2008, which claims priority from EP 07101134.0, filed Jan. 25, 2009.

FIELD OF THE INVENTION

The present invention relates to a method of predicting the quality of a polypropylene container. More specifically, the invention relates to a method of predicting the drop impact resistance of a polypropylene container.

BACKGROUND OF THE INVENTION

Stretch blow moulding (SBM) is a process of producing hollow thermoplastic articles, for example containers. This process involves the initial production of a preform article by injection blow moulding. The preform article is then subjected to biaxial orientation by axially stretching the preform using an external gripper or an internal stretch rod, and then by radially stretching it by blowing compressed air into the preform and pushing the material against a mould to form a hollow thermoplastic article.

The biaxial orientation provides the stretch blow moulded article with improved physical properties. The process aligns the molecules along two planes providing additional strength and better barrier properties than is possible using other blow moulding techniques. Other advantages include better clarity, increased impact strength, and reduced creep.

Stretch blow moulded articles can be obtained using two different stretch blow moulding processes. During the so-called "single-stage process" or "in-line process", the preform and blow moulded articles are prepared on the same machine. During the "two-stage process" or "reheat process" the preforms are formed during the first stage on an injection machine and then left to cool to ambient temperature. After this stage, the preforms may be transported from one location to another. In the second stage, the preforms are reheated and stretch blow moulded into the desired article on a reheat-blow machine. The present invention can be applied to both single-stage and two-stage stretch blow moulded containers.

There has been a long felt need in the industry of SBM manufacturing to obtain polypropylene containers, which have a high drop impact resistance. Consequently, there is also a need to develop a method, which would allow one to rapidly and easily determine the drop impact resistance of a polypropylene container.

The drop impact resistance can be determined using tests such as the standardised test D2463-95 devised by the American Society for Testing and Materials (ASTM) or the test devised by the International Society of Beverage Technologists (ISBT). However, these are long processes, which requires many containers, filling them up, conditioning them and then dropping them on a plane in several different inclinations using special drop impact resistance equipment.

US 2005/0249905 discloses a free shrinkage test, which is a method of predicting and estimating the processing parameters of a polypropylene container made by a two-stage process. This test involves measuring the wall thickness and shrinkage of a container after immersing it in a hot oil bath. It discloses carrying out free shrinkage tests for containers obtained using the two-stage stretch blow moulding process and containers consisting essentially of polypropylene random copolymer. However, it does not describe how the drop impact resistance can be obtained. In addition, carrying out repetitive tests in hot oil is neither safe, nor user-friendly.

There is thus a need to provide a rapid and easy method to predict the drop impact resistance of a polypropylene container obtained from either the one-stage or the two-stage stretch-blow moulding process.

It is therefore an aim of the present invention to provide a method to predict the drop impact resistance of a polypropylene container.

It is another aim of the present invention to provide a rapid method to predict the drop impact resistance of a polypropylene container.

It is yet another aim of the present invention to provide an easy method to predict the drop impact resistance of a polypropylene container.

Furthermore, it is an aim of the present invention to provide a method to predict the drop impact resistance of a polypropylene container obtained from a one-stage stretch-blow moulding process.

It is also an aim of the present invention to provide a method to predict the drop impact resistance of a polypropylene container obtained from a two-stage stretch-blow moulding process.

One or more of these aims has been, at least partially, fulfilled by the present invention.

SUMMARY OF THE INVENTION

The present invention is directed to a method for predicting the impact resistance of a stretch blow moulded polypropylene container (henceforth simply referred to as a polypropylene container). In accordance with the present invention, the impact resistance is predicted by measuring the shrinkage of the container after placing it in an oven.

The present invention relates in particular to a method for predicting the drop impact resistance of a stretch blow moulded polypropylene container comprising the following steps:
  a). Measuring one initial property selected from the axial length, circumference, diameter and volume of said container;
  b). placing said container in an oven wherein the temperature is below the melting temperature of the polypropylene and at least 120° C.;
  c). removing said container from said oven;
  d). remeasuring the same property as measured in step (a) of said container;
  e). calculating the percentage difference between the remeasured and initial property; and
  f). determining the drop impact resistance, which is proportional to said difference.

DETAILED DESCRIPTION OF THE INVENTION

Figure 1:
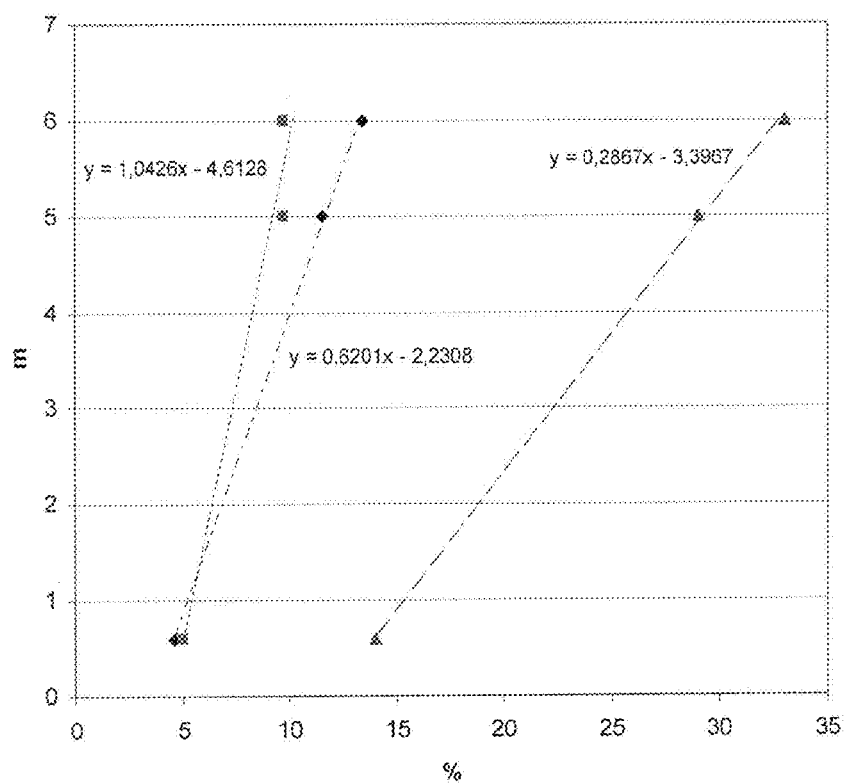
FIG. 1 is a graph showing the proportionality of the drop impact resistance to the shrinkage of the bottle.

The present invention relates to a method of predicting the impact resistance of a polypropylene container. The polypropylene container is placed in an oven at a given temperature for a given period of time, whereupon the shrinkage of the container correlates with its drop impact resistance. The more the container shrinks, the higher its drop impact resistance is.

The method applies to polypropylene containers made by stretch blow moulding, either from the one-stage or the two-stage stretch blow moulding process. Preferably, the method applies to containers obtained from the two-stage process.

The polypropylene container to which the invention applies can be of any size and shape. Examples include jars and bottles. The method preferably applies to bottles.

The axial length, circumference or volume of the container is measured before and after shrinkage. If the container has a cylindrical shape, the diameter may be measured as well. More preferably, the measured property is the volume of the container.

The percentage difference in the properties before and after placing the container in the oven is calculated according to the following formula:

$$\% \text{ difference} = 100 \times (M_0 - M)/M_0 \quad (I)$$

wherein:
$M_0$ is the measured initial axial length, circumference, diameter or volume of the container before placing it in the oven
$M$ is the measured axial length, circumference, diameter or volume of the container after removing it from the oven Any oven, which can achieve an internal temperature of at least 120° C., can be used. However, the temperature within the oven should not rise above the melting temperature of the polypropylene. The melting temperature of polypropylene is usually between 140-145° C., generally about 145° C. If the temperature within the oven is too low, no or little shrinking occurs. If the temperature within the oven is too high, the polypropylene container may start to melt. The temperature within the oven is preferably at least 120° C., more preferably about 130° C.

The residence time of the container in the oven is at least such that the inside temperature of the container becomes homogeneous with the temperature within the oven. The optimum residence time hence depends on the oven and on the container, mainly on its wall thickness, shape and size. Usually, the residence time of the container in the oven is at least 20 minutes, preferably at least 30 minutes, more preferably about 40 minutes.

The shrinkage is proportional to the drop impact resistance. This correlation will depend on the oven temperature and residence time used. If the correlation is not known, it can be determined by measuring the shrinkage of containers with known drop impact resistances. The drop impact resistance of a bottle can be measured according to the standard drop impact test devised by the ISBT or the ASTM standardised test D2463-95. Once the correlation is known for a particular oven temperature, residence time and particular property, the drop impact resistance of any polypropylene container can be predicted by calculating it from the measured shrinkage and using the predetermined correlation.

The most preferred combination of oven temperature and residence time for testing standard bottles of usual shape and size is 130° C. and 40 minutes. Using these conditions, a shrinkage of 9% in length or diameter correlates with a good drop impact resistance of 5 meters. A shrinkage of 13% in length or diameter provides a very good drop impact resistance of at least 6 meters. In terms of volume, a shrinkage of at least 33%, also indicates a very good drop impact resistance of at least 6 meters.

The containers to which this method is applicable can comprise any kind of isotactic polypropylene. Examples include propylene homopolymers, propylene-olefin random or block copolymers, and blends of polypropylene with other polyolefins. Olefins that can be used to form the copolymer or the polyolefin in the blends, include ethylene, butene, pentene, hexene and octene. Preferably, the olefin is ethylene.

The polypropylene containers to which the method is applicable are usually made from polypropylene having a melt flow index (MFI) of at most 50 g/10 minutes. Preferably, the method applies to polypropylene containers comprising polypropylene having an MFI between 1 and 30 g/10 minutes, more preferably between 1 and 10 g/10 minutes. The MFI is measured according to ASTM D-1238 (measured at 230° C.).

EXAMPLES OF THE INVENTION

The drop impact resistances of 3 different standard bottles R1, R2 and R3 were predicted using the invented method.

Firstly, the diameter of each bottle was measured at various positions. In addition, the axial length and volume of each bottle were measured as well. The empty, open bottles were then kept in an oven at 130° C. for 40 minutes. After cooling, the diameters, axial length and volume of each bottle were measured again. The percentage differences in diameter and axial length of the bottle were calculated. From the percentage differences in diameter, a mean percentage difference in diameter was determined. The results are provided in Table 1.

According to the known correlation for a residence time of 40 minutes at 130° C., if the bottles shrank by at least 9% in diameter and/or length, it was predicted that the bottles would have a good drop impact resistance i.e. at least 5 meters. Likewise, if the bottles shrank by at least 29% in volume, the same predication could be made. If the bottles shrank by less than 9% in diameter and/or length and/or by less than 29% in volume, it was predicted that the bottles would have a bad drop impact resistance i.e. less than 5 meters. Hence, according to the shrinkage of bottles R1 and R2, these should have good drop impact resistances and bottle R3 should have a bad drop impact resistance.

These predictions were then compared with the actual drop impact resistances of the bottles, measured according to an adapted version of the standard test devised by the ISBT. In this case, the test was carried out as follows. The bottles were filled to the brim with water and closed. They were then conditioned at room temperature for at least 24 hours. The plane of inclination of the surface onto which the containers were dropped was set to 15°. The drop tests were then carried out at ambient temperature from different heights. The tests were started at a height at which the bottle was suspected to break and continued in 0.5 meter intervals up to a height of 6 m or up to the height at which the bottle broke. The breaking height (i.e. drop impact resistance) was determined as the height at which a leakage, no matter how small, was observed.

As it can be seen in Table 1 below, the predictions according to the invented method correspond to the actual drop impact resistances. Examples R1 to R3 are bottles made of propylene-ethylene random copolymer having a melt flow index of 10 g/10 min, an ethylene content of 3.3% by weight and nucleating or clarifying agents. FIG. 1 shows the proportionality of the shrinkage in terms of diameter, height and volume to the drop impact resistance. The x-axis represents the percent shrinkage and the y-axis the drop impact resistance in meters.

TABLE 1

| Examples | R1 | R2 | R3 | Symbol in FIG. 1 |
|---|---|---|---|---|
| Preform melt temperature/° C. | 240 | 270 | 235 | |
| Mean percentage difference in diameter after shrink test/% | 13.40 | 11.50 | 4.60 | Diamond |

TABLE 1-continued

| Examples | R1 | R2 | R3 | Symbol in FIG. 1 |
|---|---|---|---|---|
| Percentage difference in axial length after shrink test/% | 9.70 | 9.70 | 5.0 | Square |
| Percentage difference in volume after shrink test/% | 33 | 29 | 14 | Triangle |
| Drop impact resistance at room T °/m | 6.0 | 5.0 | 0.6 | |

The invention claimed is:

1. A method for predicting drop impact resistance of a stretch-blow molded polypropylene container, comprising:
determining a correlation between shrinkage and drop impact resistance for a known container for an oven,
measuring one initial property selected from axial length, circumference, diameter and volume of the propylene container;
placing the propylene container in the oven, wherein a temperature of the oven is below a melting temperature of the polypropylene and is at least 120° C.;
removing the propylene container from the oven;
remeasuring the same property of said propylene container;
calculating a percentage difference between the remeasured and initial property; and
determining the drop impact resistance from the percentage difference and the correlation.

2. The method of claim 1, wherein the oven temperature is at least about 130° C.

3. The method of claim 1, wherein a residence time of the container in the oven is at least 20 minutes.

4. The method of claim 1, wherein a residence time of the container in the oven is at least 30 minutes.

5. The method of claim 1, wherein the initial property is the volume of the container.

6. The method of claim 1, wherein the polypropylene has a melt flow index of at most 50 g/10 min (ASTM D-1238 at 230° C.).

7. The method of claim 1, wherein the polypropylene has a melt flow index of between 1 and 10 g/10 min.

8. The method of claim 1, wherein the correlation is dependent upon temperature, residence time, and/or property.

9. The method of claim 1, wherein the container comprises a polypropylene selected from propylene homopolymer, propylene-olefin block copolymer, random copolymer, blends of polypropylene and a polyolefin and combinations thereof.

10. The method of claim 9, wherein the container consists essentially of propylene-ethylene random copolymer.

* * * * *